United States Patent [19]

Solazzo

[11] Patent Number: 4,990,133
[45] Date of Patent: Feb. 5, 1991

[54] REMOVABLE J-J URETERAL STENT

[75] Inventor: Anthony Solazzo, Warren Township, Somerset County, N.J.

[73] Assignee: Tenax-Glynn Corporation, Flemington, N.J. ; a part interest

[21] Appl. No.: 503,277

[22] Filed: Apr. 2, 1990

[51] Int. Cl.$^5$ .................... A61M 5/00; A61M 5/178; A61M 25/00
[52] U.S. Cl. ...................... 604/8; 604/165; 604/280
[58] Field of Search ..................... 604/8–10, 604/164, 165, 280–282, 54

[56] References Cited

U.S. PATENT DOCUMENTS

| | | | |
|---|---|---|---|
| 3,890,977 | 6/1975 | Wilson | 604/281 |
| 4,596,564 | 6/1986 | Spetzler et al. | 604/281 |
| 4,747,833 | 5/1988 | Kousai et al. | 604/164 |
| 4,790,809 | 12/1988 | Kuntz | 604/8 |
| 4,790,810 | 12/1988 | Pugh, Jr. et al. | 604/8 |

Primary Examiner—Robert A. Hafer
Assistant Examiner—Michael Brown
Attorney, Agent, or Firm—Kenneth P. Glynn

[57] ABSTRACT

The present invention is directed to a ureteral catheter stent which includes an elongated, relatively flexible, hollow tubular member having a plurality of drainage openings extending through a wall thereof and having two end portions each end portion being in the form of a hook and having at least one male and/or female interlocking unit formed into the end of at least one hook. The ureteral catheter stent of the present invention is used in conjunction with a follower which is interlocked therewith during insertion so that rotation or movement of the follower will create exact rotation of the stent on the guide wire during insertion so as to accurately and easily enable the user to place the hook of the stent in the direction desired. Additionally, the ureteral catheter stent of the present invention may have other sources for inserting other devices, rods, tubes of the like into the stent at a future date, without having to locate the lower end of a hook and without having to straighten the hook itself. This is achieved by including at least one segment of wire made of a memory material embedded into the wall of the tubular member for a distance of at least one end portion and at a location which is coincidental with the inside radius of the hook and also providing at least one cut through at least sixty percent (60%) of the tubular member at a location away from said wire and opposite thereto. With this mechanism, a user may, at some date after the insertion of the stent, push aside the hook or J end, utilizing the wire as a hinge and the slit as a door to expose the stent to a straight line use.

8 Claims, 2 Drawing Sheets

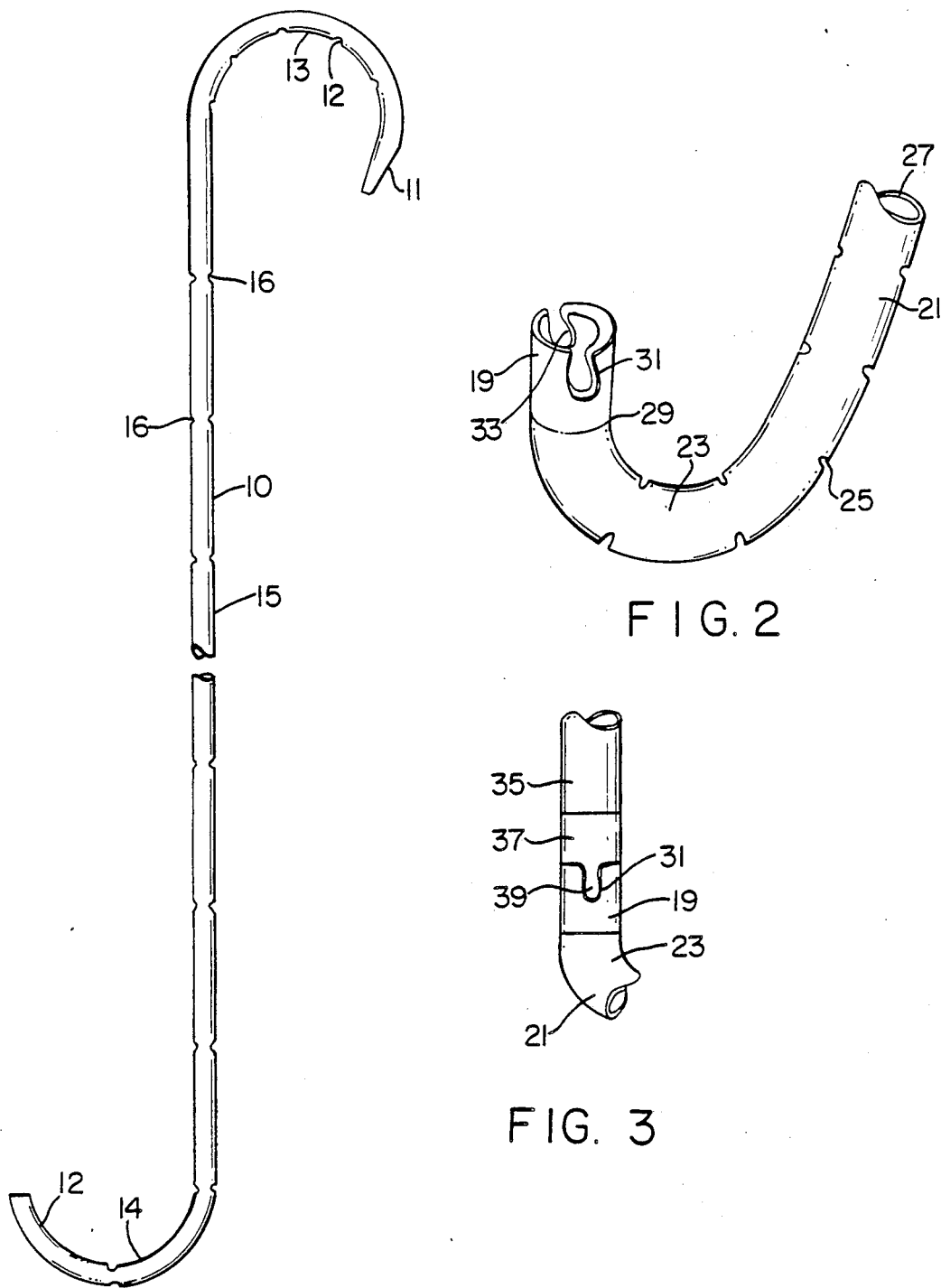
FIG. 2
FIG. 3
PRIOR ART
FIG. 1

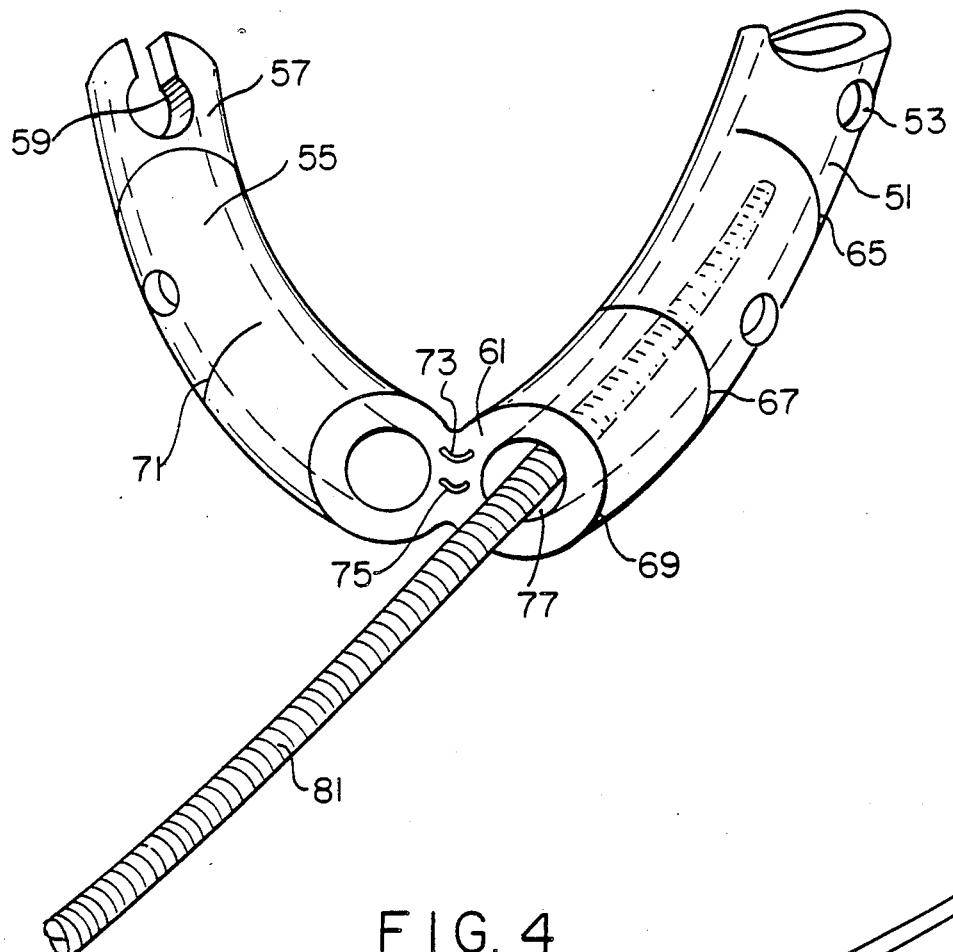
FIG. 4
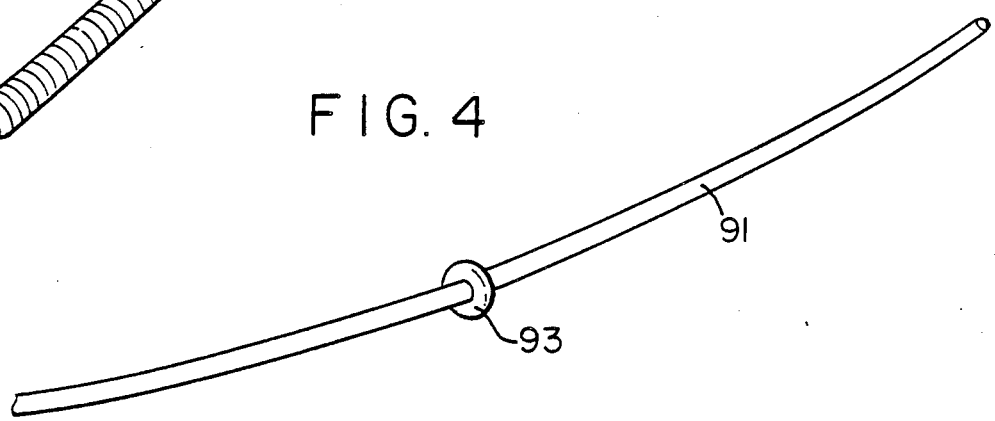
FIG. 5

REMOVABLE J-J URETERAL STENT

BACKGROUND OF THE INVENTION

1. Field of the Invention

The present invention is directed to a urethral catheter stent which uses a double J arrangement. The double J is basically a flexible stent for irrigation with a hook at each end forming a J at each end. The present invention is directed to an improved stent of the double J type which provides for the ability of the inserting physician to controllably rotate the stent during insertion, and, also, enables controlled reentry into the stent for various purposes.

2. Prior Art Statement

Various types of catheters have been available for many decades and are important to the survival of some patients. For example, U.S. Pat. No. 2,393,003 describes a kidney catheter wherein a flexible rod made of metal or any suitable material is used to stiffen a otherwise soft catheter to enable a urologist to direct the catheter up into the kidney. This particular patent teaches the use of a hook on the handle of a rod which attaches to a tongue at the end of the catheter so as to maintain it in a stretched position during insertion, i.e., to prevent it from sliding off or folding or otherwise creating difficulties during insertion.

Ureteral catheter stents were developed as drainage tubes to bypass urethral obstructions or ureterovaginal fistulas so as to maintain urinary drainage. Prior art stents have been made of flexible materials and are usually hollow elongated members with irrigation orifices throughout all or part of the length of the stent. Stents may be fully open ended at both ends or open at only one end, depending upon the method of insertion and ultimate purpose. U.S. Pat. No. 4,212,304 to Roy Finney describes a catheter which has proximal and distal ends which are in the form of hooks. These hooks are sometimes referred to as J stents or double J stents. These types of stents are straightened for introduction into the body passage by the insertion of a wire stylet into the lumen of the stent and the stent is provided with some sort of indicating means to show the direction of the proximal hook so that the surgeon inserting same will know approximately the direction of the proximal hook when the stylet is removed so that proper placement is enhanced.

U.S. Pat. No. 4,787,884 to Jay Goldberg describes a dual wire guide system for inserting ureteral stents and particularly the double J type stents. In this patent, the pusher wires open at both ends and sized to fit into the lumen of the stent. The leading end of the pusher wire has a diameter greater than the reduced opening in the stent and the guide wire is sized to fit within the lumen of the pusher wire and has a leading end which is smaller in diameter than the reduced opening of the stent. The retaining member keeps the leading end of the guide wire from leaving the lumen of the pusher wire when an obstruction is encountered in the ureter, the retaining member is disengaged and the leading end of the guide wire is passed through the reduced opening and maneuvered passed the obstruction. The pusher wire and stent then can be advanced over the guide wire passed the obstruction.

Notwithstanding the prior art, it is believed that the present invention improved double J stent affording the user the ability to control the rotation or movement of the stent during insertion both with accuracy and with ease as well as assuring the opportunity for future use of the stent, is neither taught nor rendered obvious in the prior art.

SUMMARY OF THE INVENTION

The present invention is directed to a ureteral catheter stent which comprises an elongated, relatively flexible, hollow tubular member having a plurality of drainage openings extending through a wall thereof and having two end portions each end portion being in the form of a hook and having at least one male and/or female interlock unit formed into the end of at least one hook. The ureteral catheter stent of the present invention is used in conjunction with a follower which is interlocked therewith during insertion so that rotation or movement of the follower will create exact rotation of the stent on the guide wire during insertion so as to accurately and easily enable the user to place the hook of the stent in the direction desired. Additionally, the ureteral catheter stent of the present invention may have means for inserting other devices, rods, tubes of the like into the stent at a future date, without having to locate the lower end of a hook and without having to straighten the hook itself. This is achieved by including at least one segment of wire made of a memory material embedded into the wall of the tubular member for a distance of at least one end portion and at a location which is coincidental with the inside radius of the hook and also providing at least one cut through at least sixty percent (60%) of the tubular member at a location away from said wire and opposite thereto. With this mechanism, a user may, at some date after the insertion of the stent, push aside the hook or J end, utilizing the wire as a hinge and the slit as a door to expose the stent to a straight line use.

BRIEF SUMMARY OF THE DRAWINGS

The present invention will be more fully understood when the specification herein is taken in conjunction with the appended drawings, wherein:

FIG. 1 shows a front view of a prior art stent;

FIG. 2 shows a J or hook end of a present invention stent which includes two interlock units;

FIG. 3 shows a cut portion of a present invention stent in its interlocked position with a follower;

FIG. 4 shows a frontal oblique view of another embodiment of the present invention stent wherein a slit in the hook end has been opened for insertion of a guide wire; and, FIG. 5 shows a retrograde pyelogram catheter which may be inserted via the stent shown in FIG. 4 when that stent is already in place in the patient.

DETAILED DESCRIPTION OF THE PRESENT INVENTION

As mentioned above in discussing the prior art, stents are inserted by being first put on a guide wire and then passed up through the ureteral to the kidney for drainage for the purpose of opening up a problematic ureteral and/or bypassing obstructions. FIG. 1 shows a front view of a prior art double J stent. In this prior art embodiment, stent 10 has drainage orifices 16 and a straight, middle section 15. It is comprised of a hollow flexible, elongated tubular material and has end portions 13 and 14 in the form of hooks or J shapes. Distal end 12 has a normal opening and, in this embodiment, proximal end 11 is slightly closed. A guide wire is inserted in distal end 12 and straightens hook 14. The guide wire passes up through straight section 15 and straightens end portion hook 13 and stops before extending through proximal end 11. Other prior art embodiments may have proximal end 11 totally closed off in stead of tapered as shown.

The difficulty with inserting the prior art stent 10 involves the ability of the surgeon inserting this to be able to effectively rotate or move it. Generally, the guide wire is much longer than the stent itself and prior to completing insertion, the stent is out of view and out of reach from the surgeon. Typically, a flexible hollow follower may be located on the guide wire behind the stent and this is used to hold the stent at a selected distance into the patient while the guide wire is removed therefrom. Nonetheless, the ability to rotate or move a prior art stent depends at least in part on whether or not the guide wire remains in frictional contact, at least the proximal end of the stent so as to enable simultaneous rotation of the guide wire and the stent. If the guide wire rotates freely or slips, location is then totally dependent upon radiant energy markings and the like for location.

The present invention is directed to a technique for eliminating the difficulties and chance for error in rotating the stent to properly place the hooks once the stent distance into the patient has been determined. Referring now to FIG. 2, there is shown a present invention stent 21 being truncated at cut off 27 and having a distal end 23 in the form of a hook. Irrigation ports such as port 25 is shown. At the end 29 of the hook of distal end 23 is a permanently attached or integrally formed interlocked segment 19 which, in this case, includes two female interlock units 31 and 33 as shown. A single interlock unit could be used or three or more could be used and they may be male or female or a combination thereof. FIG. 3 shows a portion of present invention stent 21 at its distal end 23 with like parts like numbered. FIG. 3 also shows a portion of follower 35 which has an interlock segment 37 with male interlock unit 39 inserted into female interlock 31 as shown.

The stent and follower of the present invention are used as in the prior art except that, due to the interlock feature, exact rotation and manipulation of the stent is achieved by external rotation or movement of the follower by the surgeon. Disengagement of the male/female connection is then made by first withdrawing the guide wire after proper placement or location of the stent is achieved. Then separation occurs due to a natural tendency of the lower J section of the stent to reshape into a hook form (memory) thereby separating away from the male pusher connection.

In addition to the foregoing, the present invention stent may alternatively or additionally include the use of one or more wires made of memory material which are inserted or embedded into the wall of the stent and by also providing cut segments in the stent so as to enable the distal end of the stent to be opened, i.e. so that the J end or hook can be pushed away with the wire being used as a hinge for the direct, straight line insertion of subsequent devices for use by the surgeon.

Thus, referring now to FIG. 4, there is shown stent 51 with drainage orifices such as drainage orifice 53. Distal end 55 is typically a hook end and includes an interlock segment 57 with interlock unit 59, in this case a female interlock unit, as shown. Embedded into the wall 61 of stent 51 are wires 73 and 75 as shown. They are made of memory materials so that when used in conjunction with preformed slits such as slits 65, 67, 69 and 71, the distal end 55 may be pushed away so as to create a straight line opening such as opening 77, as shown. By this mechanism, the surgeon may use a guide wire to relocate or to clear the stent or other servicing may be used. Also, subsequent operations may be performed such as with retrograde pyelogram catheter 91 and stop 93 as shown in FIG. 5.

Although the drawings described above illustrate interlock units with male or female "picture puzzle" type of configurations, it should be noted that other types of interlocks may be utilized without exceeding the scope of the present invention. For example, cut outs in the form of a J hook or a bat and ball or a square or diamond or other type of flat surface interlocking arrangement could be used. Additionally, the stents themselves are made of conventional materials which prior art stents have been made of but the interlock unit portion could be made of the same material or stiffer material such as teflon or the like. The wires which are made of memory material may be metal or synthetic material and may be flat, round, oval or of any other configuration. The cuts located at the J hook area are at least sixty percent (60%) cut across the axis of the stent and these are cut into the stent, as shown in the drawings, at a position opposite the wires so that the hinging effect is achieved as shown in the figure. A single wire may be used or a plurality of wires may be used and the term "wire" as used herein should be broadly interpreted to be any material which will function as described. Further, the wire should be inserted at least into the straight section from the J portion and could extend about twenty five percent (25) of the total length of the stent, although longer lengths could be used. However, in the case when longer wires are utilized in excess of twenty five percent (25%) of the length of the stent, such wires would only act to stiffen the stent and not provide any additional functionality to the hinging aspect which is the purpose set forth herein. The irrigation orifices may be located in any reasonable manner along the stent and the exact shape and length of the J sections as well as the exact length of the stent itself are already within the purview of the artisan. Likewise, the particular guide wire or guide wire and wire guide wire cover arrangement may be those which are conventionally available. The pusher which interlocks with the stent of the present invention may be made of teflon or other material and, but for the addition of the interlock unit portion, would be substantially the same as the prior art type of pushers.

Obviously, numerous modifications and variations of the present invention are possible in light of the above teachings. It is therefore understood that within the scope of the appended claims, the invention may be practiced otherwise than as specifically described herein.

What is claimed is:

1. An ureteral catheter stent, which comprises: an elongated relatively flexible hollow tubular member having a plurality of drainage openings extending through a wall thereof and having two end portions, each end portion being in the form of a hook, and at least one hook being separate and attachable to said elongated member and having at least one of a male or female interlock unit at the end of said hook and the other of said male or female interlock unit at the end of said elongated member; and, further, wherein the flexibilty of said tubular member is such that said interlock unit is formed so as to functionally engage in an interlocking fashion with the corresponding male or female interlock unit of a separate hook only when a stiff rod in inserted into said hook and said elongated relatively flexible hollow tubular member.

2. The stent of claim 1 wherein two male or female interlock units are located at the end of at least one hook.

3. An ureteral catheter stent, which comprises: an elongated relatively flexible hollow tubular member having a plurality of drainage openings extending through a wall thereof and having two end portions, each end portion being in the form of a hook, and having at least one segment of wire made in a memory material embedded within the wall of said tubular member for a distance of at least one end portion and at a location which is coincidental with an inside radius of said hook of said end portion and having at least one cut through at least sixty percent (60%) of said tubular member at a location away from said wire; and further includes at least one of a male or female interlocking unit at the end of the hook being cut and the other of a male or female interlocking unit at the end of said elongated member at said cut; and further, wherein the flexibility of said tubular member is such that said interlock unit is formed so as to engage in an interlocking fashion functionally with the corresponding male or female interlock unit of a separate hook only when a stiff rod is inserted into said elongated, relatively flexible hollow tubular member.

4. The stent of claim 3 wherein said wire made of memory material is a round memory metal.

5. The stent of claim 3 wherein said wire made of memory material is a flat memory metal.

6. The stent of claim 3 wherein said wire made of memory material is a synthetic fiber.

7. The stent of claim 3 wherein two strands of said wire made of memory material are embedded within the wall of said hollow member.

8. The stent of claim 3 wherein said wire extends within said tubular member a distance of not more than twenty-five percent (25%) of the entire length of said member.

* * * * *